United States Patent [19]

Razzano et al.

[11] Patent Number: 5,229,121

[45] Date of Patent: Jul. 20, 1993

[54] METHOD FOR CAMOUFLAGING A HUNTER

[76] Inventors: Thomas Razzano, 92 George St.; Thomas Noto, 14 Ridge Rd., both of South River, N.J. 08882

[21] Appl. No.: 699,663

[22] Filed: May 14, 1991

[51] Int. Cl.$^5$ ............................................. A61K 7/021
[52] U.S. Cl. ................................. 424/401; 132/200; 424/63; 428/919
[58] Field of Search ............... 427/262, 265, 280, 155; 428/919; 424/63, 401, 78.03; 132/200

[56] References Cited

U.S. PATENT DOCUMENTS

| | | | |
|---|---|---|---|
| 4,665,107 | 5/1987 | Micale | 424/401 X |
| 4,690,653 | 9/1987 | Goldberg | 446/27 |
| 4,783,350 | 11/1988 | DeMatteo et al. | 428/919 X |
| 4,837,056 | 6/1989 | Easley | 427/262 |

OTHER PUBLICATIONS

Cabela's Fall 1990 Catalog, front & back cover and pp. 22, 30 and 138, fall 1990, Sidney, Nebraska.
P.G.S. Archery Co. 1991 Catalog, pp. 1, 2, 61 and 62, 1991, Vineland, New Jersey.
Sport Shop 1990 Catalog, front & back cover and pp. 2, 38, 40 and 55, 1990, Grifton, North Carolina.
Gander Mountain Fall/Winter 1990 Catalog, front & back cover and pp. 9, 27, 28 and 128, 1990, Wilmot, Wisconsin.
Imagineering 1991 Halloween Catalog, front and back cover and p. 8, 1991, Phoenix, Arizona.
Second Skin Liquid Latex Product Label, front and back of label, 1989, Phoenix, Arizona.

*Primary Examiner*—Evan Lawrence

[57] ABSTRACT

A hunter's face is camouflaged by applying colored fluids which dry to form a peelable film. The fluids are used to produce a camouflage pattern which comprises splotches or stripes having colors comprising black, brown, green, yellow, white and gray. In addition, the camouflage pattern can be formed by applying colored fluids over a base layer of peelable film. The camouflage is easily removed by peeling it off the hunter's face.

20 Claims, 2 Drawing Sheets

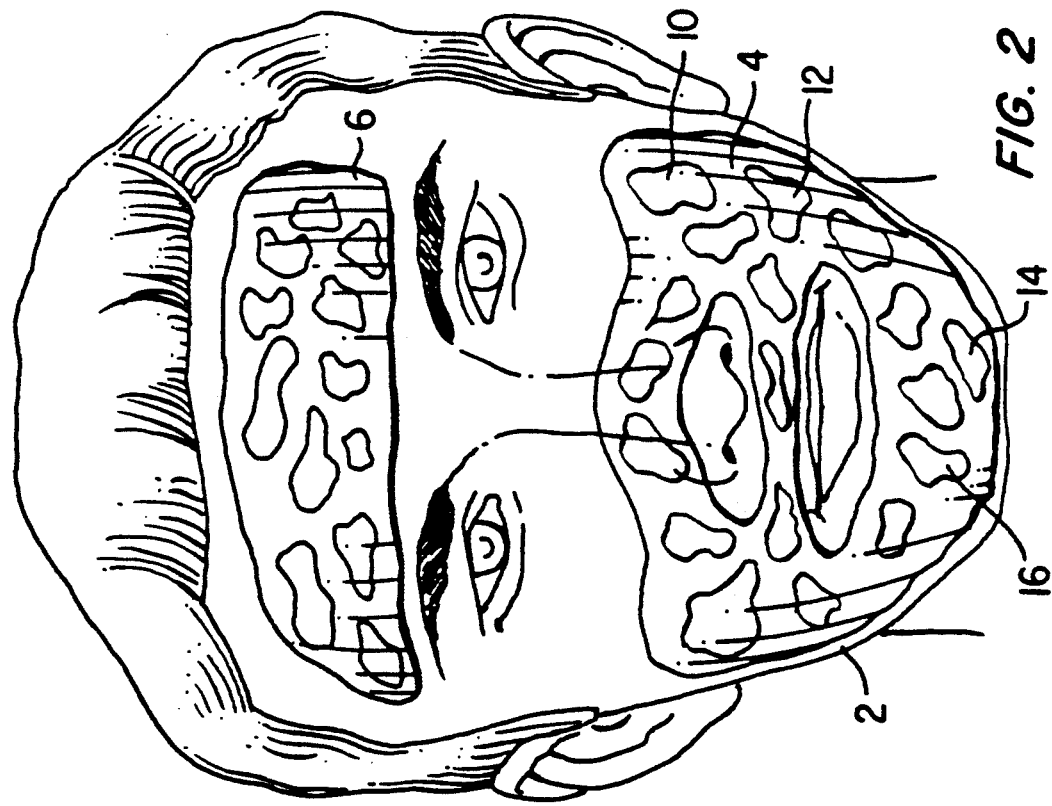
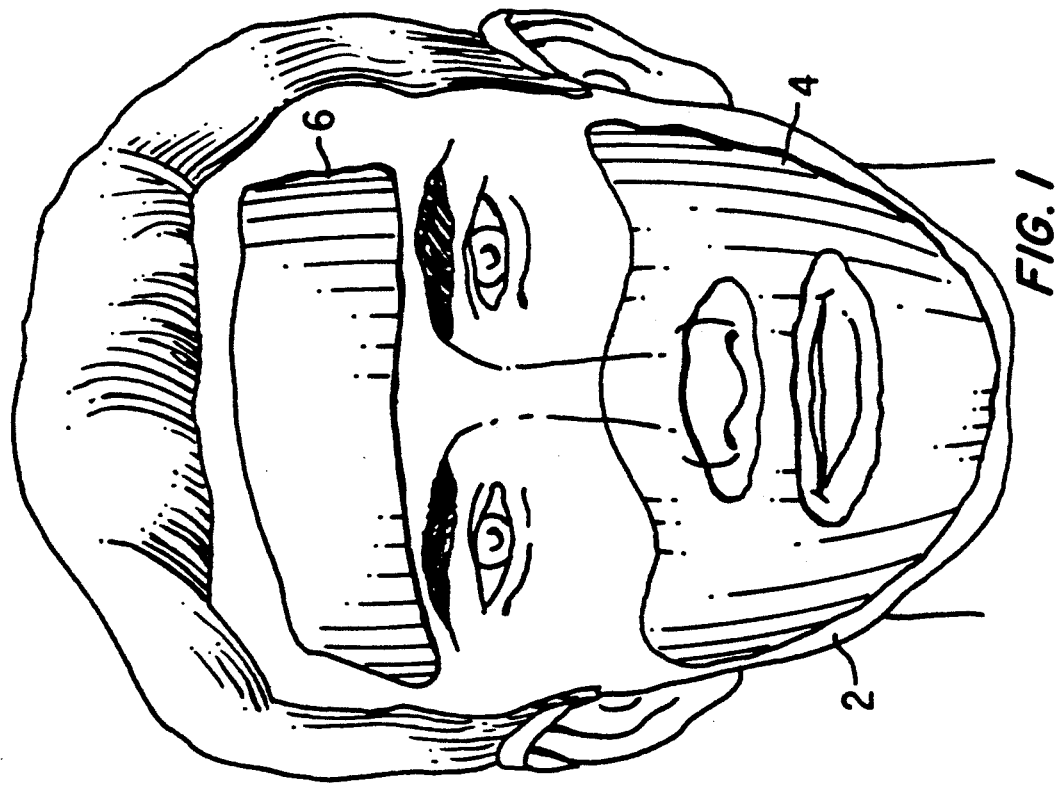

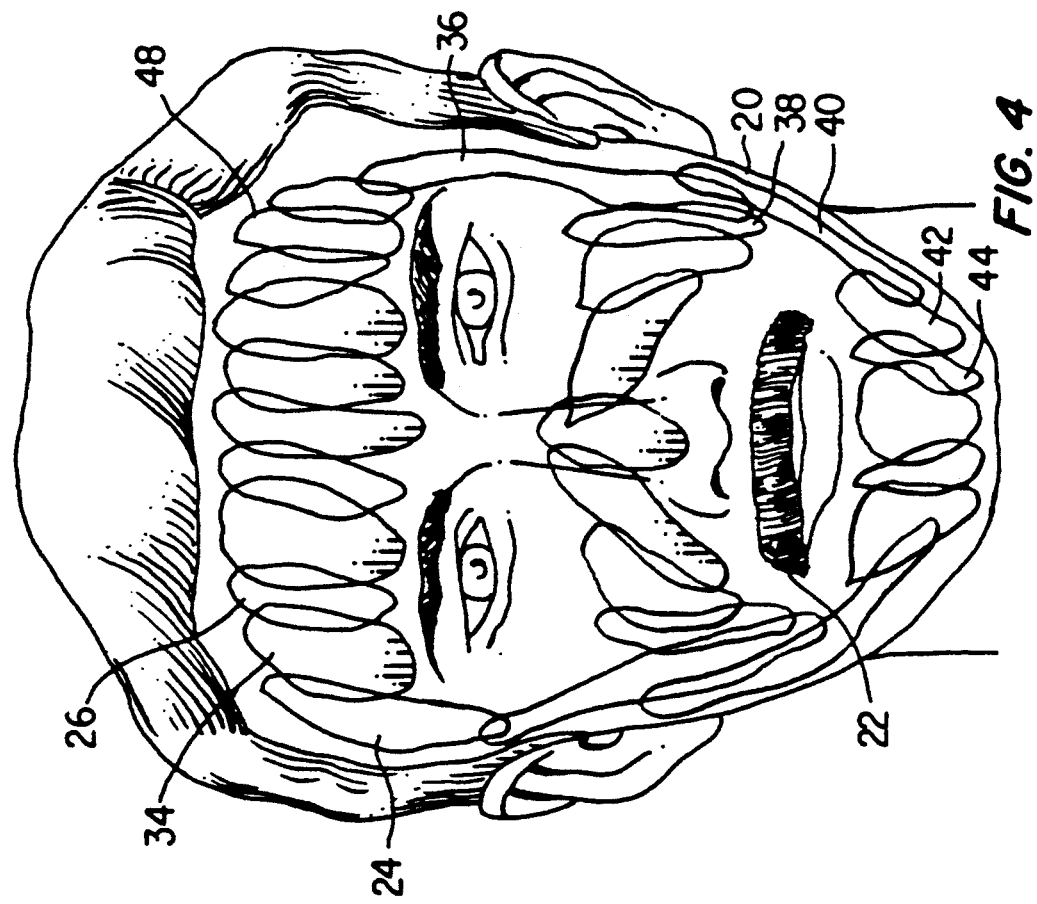
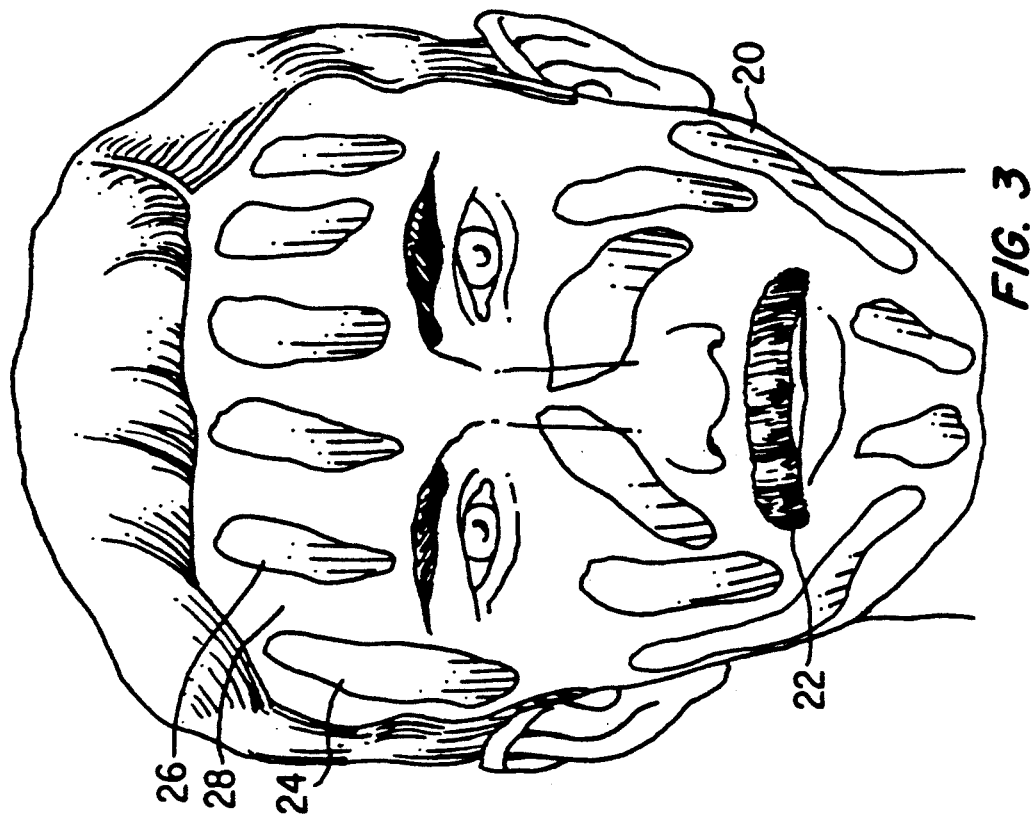

METHOD FOR CAMOUFLAGING A HUNTER

BACKGROUND OF THE INVENTION

1. Field of the Invention

The invention relates to the field of hunting. In particular, it relates to camouflaging a hunter so that it is less likely that the hunter will be detected by game.

2. Description of the Related Art

Existing camouflaging techniques involve creating a camouflage pattern on the area to be camouflaged using colored creams or powders. The creams and powders are available in colors such as black, brown, green or gray. The areas that are camouflaged in this manner are usually located on the hunter's face.

Camouflage creams are uncomfortable to wear, clog pores, smear easily and are difficult to remove. Creams are uncomfortable to wear because they feel oily and greasy. Using creams can clog pores and lead to skin problems such as acne or blackheads. Creams also perform poorly by smearing easily when accidently touched. In addition, creams are difficult to remove. Removing cream involves using premoistened towels or a washcloth with soap and water. Even after a great deal of effort, it is not unusual for a thin layer of cream to remain on the hunter's face. The remaining cream is unsightly and clogs pores. Removing the remaining thin layer of cream often requires scrubbing so hard that the underlying skin becomes irritated or raw.

Camouflage powders have several disadvantages. The powders are almost as difficult to remove as creams, and they are smeared by rain or perspiration. Given that hunters sometimes hunt in rainy or warm weather, it is likely that the camouflage powder will smear and provide less camouflage for the hunter, and thereby increase his probability of being detected by game. In addition, powders are difficult to apply under windy conditions.

SUMMARY OF THE INVENTION

The invention involves a method for camouflaging a hunter by applying a fluid, which has a first color and dries to form a peelable film, to the area to be camouflaged, and by applying a fluid, which has a second color and dries to form a peelable film, to the area to be camouflaged.

The present invention provides a camouflage that does not feel oily or greasy, and is comfortable to wear. The resulting camouflage does not smear, and therefore does not increase the hunter's probability of being detected by game in rainy or warm weather. The camouflage provided by the invention peels off easily, and does not require the use of premoistened towels, or washcloths with soap and water. In addition, the camouflage peels off cleanly and does not leave an unsightly layer that can clog pores.

BRIEF DESCRIPTION OF THE DRAWINGS

FIG. 1 illustrates a hunter's face with a latex base layer.

FIG. 2 illustrates a hunter's face with a splotched camouflage pattern applied over the base layer of FIG. 1.

FIG. 3 illustrates a hunter's face with an initial set of camouflage stripes.

FIG. 4 illustrates a hunter's face with additional camouflage stripes placed in the spaces between the stripes of FIG. 3.

DESCRIPTION OF THE PREFERRED EMBODIMENT

The invention involves applying a camouflage pattern to exposed skin using a latex fluid or any other fluid that dries to form a film or thin sheet that can be peeled off the surface on which it has dried. However, it is preferable to use a latex fluid. The latex is in the form of a fluid that has a viscosity that can vary between that of a free flowing liquid and a thick paste. It is preferable to use a latex that has the viscosity of a thin paste similar to tooth paste. The latex can be obtained in jars, tubes and a variety of other containers, but tubes are preferable because of their convenience. It is preferable to use a precolored latex fluid to apply the camouflage. A large variety of colors can be used, but the colors should be chosen to facilitate the hunter in blending into the surrounding environment. It is preferable to use colors such as black, brown, green, white or gray. It is also possible to use the various shades, or even mixtures of the aforementioned colors.

The areas to be camouflaged typically involve the hunter's face, but they can include other areas such as his hands and neck. The area to be camouflaged should be clean and dry. The latex fluid should not be applied on areas that have hair. Once the latex fluid dries in the hair, removing the latex usually requires removing the hair. If the latex is put on facial or body hair, the latex should be thoroughly rinsed out with warm water before the latex fluid dries. The rinsing should be done immediately because the latex fluid has an average drying time of approximately two minutes. The latex fluid should not be allowed to contact the eyes, if it does, the eye should be thoroughly rinsed for fifteen to twenty minutes and medical attention should be sought. In addition, the latex fluid should not be used if the camouflaged skin displays a sensitivity to the latex.

The container in which the latex fluid is stored should be shaken before the latex is dispensed. The latex fluid can be applied to the area to be camouflaged using a finger or a tool such as a tongue depressor. It is also possible to dispense the latex fluid onto a surface where it can be mixed with a latex of a another color before being applied to the skin. In this manner different latex colors can be mixed to create custom colors.

The latex fluid can be applied in any manner, but it is preferable to use single even strokes to create a camouflage pattern on the area to be camouflaged. A camouflage pattern comprises any pattern that facilitates the hunter in blending in to his surroundings so that it is less likely that he will be detected by game. It is preferable to use splotched or striped type camouflage patterns. A splotched pattern comprises patterns such as irregular shapes or shapes with a generally roundish or oval perimeter that mimic the shape of foliage. A striped camouflage pattern comprises stripes that can be oriented in any direction, but it is preferable to use a vertical orientation that mimics the pattern of tree bark.

The aforementioned camouflage patterns can be created using one color latex fluid, or by using many different colored latex fluids. It is preferable to use colors that match the environment in which the hunter will be hunting. In choosing colors it is helpful to consider the type of vegetation in the hunting area and the season of the year.

FIGS. 1 and 2 illustrate a technique for applying a camouflage pattern in which a first latex fluid is used as a base over which one of more other latex fluids are applied.

FIG. 1 shows hunter's face 2, with latex base layer 4 applied to the areas to be camouflaged. A colorless or any color latex fluid can be used to create base layer 4. The latex fluid is applied to create base layer 4 using single even strokes. Base area 4 can comprise a single integral piece of dried latex fluid, or it can comprise several integral pieces of dried latex fluid. For example latex base layer 6, which covers the forehead of hunter's face 2 can be a separate piece of dried latex as seen in the figure, or it can be made integral to base layer 4. After allowing the base layer or layers to dry, a second latex fluid is applied over the base layer or layers to form a camouflage pattern.

FIG. 2 shows a splotched camouflage pattern applied over base layers 4 and 6, however a striped pattern or any other pattern that facilitates the hunter in blending into the environment can be used. The camouflage pattern is applied over the base layer with single even strokes preferably using a latex fluid having a different color than the color of the base layer, however any color may be used. It is most preferable to use a variety of colors in the camouflage pattern. For example, splotched pattern 10 can be green, splotched pattern 12 can be black, splotched pattern 14 can be brown, and splotched pattern 16 can be yellow. Other colors or mixtures of colors may be used, but it is preferable to use colors that will match the hunter's hunting environment. Once the latex making up the camouflage pattern has dried, the camouflaged area can be touched without smearing the camouflage pattern.

Since base layers 4 and 6 are peelable films, it is not necessary to create a camouflage pattern on top of the base layers using a fluid that dries to form a peelable film. Any fluid which has a color that facilitates the hunter in blending into his surroundings can be used. It is preferable to use a fluid that dries to form a camouflage pattern which does not smear.

FIGS. 3 and 4 illustrate another technique for camouflaging an area. This technique involves placing striped camouflage patterns to the area to be camouflaged without using a base layer. The figures illustrate a striped pattern, however a splotched pattern or any other pattern that facilitates the hunter in blending into the environment can be used.

In FIG. 3, hunter's face 20 has mustache 22. In this situation, the latex fluid should not be place in mustache 22. The dried latex is very difficult to remove from body or facial hair and removing the dried latex usually involves removing the hair in which it is located.

Camouflage stripes are applied to hunter's face 22 using single even strokes. The stripes are preferably oriented in a vertical direction and are somewhat parallel to each other. The stripes can be applied adjacent to each other, but it is preferable to leave a space between adjacent stripes until the latex fluid has dried. For example, stripe 24 is applied while stripe 26 is still wet, but space 28 is left between the stripes so that applying a subsequent stripe does not smear or otherwise interfere with the previous stripe's drying. The stripes can be made using only one color latex or they can be made using a variety of latex colors or a mixture of colors.

FIG. 4 illustrates filling in the spaces between stripes with other stripes. After the stripes of FIG. 3 have dried, the spaces between the stripes can be covered with additional latex stripes. For example, space 28 is covered by latex stripe 34. Additional stripes should be added until all of the spaces between the initial set of stripes are covered. It is preferable to slightly over lap the first set of stripes with the second set of stripes so that no spaces are left between adjacent stripes. This results in a better camouflage pattern, and facilitates removing the camouflage by forming larger continuous pieces of latex rather than many individual pieces. A single latex color can be used to cover the spaces, but it is preferable to use more than one latex color. Once the latex making up the camouflage pattern has dried, the camouflaged area can be touched without smearing the camouflage pattern.

The resulting camouflage pattern can comprise stripes of the same color or different colors, but it is preferable that adjacent stripes have different colors. For example, stripe 36 can be green, stripe 38 can be brown, stripe 40 can be black, stripe 42 can be yellow, and stripe 44 can be gray. As with all of the prior illustrations and examples, the listed colors are mentioned as examples and are not intended to limit the scope of the invention. Any other color or mixture of colors can be used to create the aforementioned camouflage patterns.

The camouflage can be removed by carefully peeling off the dried latex. It is preferable to begin peeling off the latex starting at a border area such as area 48. In this manner, the camouflage can be easily and completely removed in the field without the use of cleansers.

Any type of latex fluid can be used to camouflage an area, but it is preferable to use a colored latex fluid available from Creative Images, Inc., 6025 West Monroe, Phoenix, Ariz. 85043. The telephone number for Creative Images Inc. is 602-269-9391. The latex fluid is sold in ½ oz. tubes and is available in a variety of colors comprising black, brown, gray and green.

The latex fluid from Creative Images, Inc. comprises Natural Latex and Ammonia, and may comprise Titanium Dioxide and Iron Oxides.

Other fluids may be used in place of a latex fluid. Any fluid that dries to form a peelable film can be used. A peelable film comprises a film or thin sheet of any material that can be peeled off the surface on which it has dried. As with the latex fluid, these other fluids can have a viscosity that varies between that of a free flowing liquid and a thick paste.

We claim:

1. A method for camouflaging a hunter, comprising the steps of:
    (a) applying a first fluid, which has a first color and dries to form a peelable film, to the area of exposed skin to be camouflaged;
    (b) applying a second fluid, which has a second color and dries to form a peelable film, to the area of exposed skin to be camouflaged to form a camouflage pattern; and
    (c) allowing said fluids to dry.

2. The method of claim wherein said step of applying said second fluid forms a striped camouflage pattern.

3. The method of claim 2, wherein said first color is a color selected from the group consisting of black, brown, green, yellow, white and gray.

4. The method of claim 1, wherein said step of applying said second fluid forms a splotched camouflage pattern.

5. The method of claim 4, wherein said first color is a color selected from the group consisting of black, brown, green, yellow, white and gray.

6. The method of claim 1, wherein said first and second fluids are latex fluids.

7. The method of claim 6, wherein said step of applying said second fluid forms a striped camouflage pattern.

8. The method of claim 6, wherein said step of applying said second fluid forms a splotched camouflage pattern.

9. The method of claim 8, wherein said first color is a color selected from the group consisting of black, brown, green, yellow, white and gray.

10. A method for camouflaging a hunter, comprising the steps of:
    (a) applying a first fluid, which dries to form a peelable film, to the area of exposed skin to be camouflaged to form a base;
    (b) applying a second fluid having a color over said base to form a camouflage pattern; and
    (c) allowing said fluids to dry.

11. The method of claim 10, wherein said step of applying said second fluid forms a striped camouflage pattern.

12. The method of claim 11, wherein said color is a color selected from the group consisting of black, brown, green, yellow, white and gray.

13. The method of claim 10, wherein said step of applying said second fluid forms a splotched camouflage pattern.

14. The method of claim 13, wherein said color is a color selected from the group consisting of black, brown, green, yellow, white and gray.

15. The method of claim 10, wherein said first fluid is a latex fluid.

16. The method of claim 15, wherein said step of applying said second fluid forms a striped camouflage pattern.

17. The method of claim 15, wherein said step of applying said second fluid forms a splotched camouflage pattern.

18. The method of claim 17, wherein said color is a color selected from the group consisting of black, brown, green, yellow, white and gray.

19. A method for camouflaging a hunter, comprising the steps of:
    (a) applying a first latex fluid having a first color to the area of exposed skin to be camouflaged to form stripes, wherein said first color is a color selected from the group consisting of black, brown, green, yellow, white and gray;
    (b) applying a second latex fluid having a second color adjacent to said stripes to form a striped camouflage pattern, wherein said second color is a color selected from the group consisting of black, brown, green, yellow, white and gray; and
    (c) allowing said fluids to dry.

20. The method of claim 19, further comprising the step of applying a third latex fluid having a third color to the area to be camouflaged to form stripes.

* * * * *